United States Patent
Panin

(10) Patent No.: US 11,039,991 B2
(45) Date of Patent: Jun. 22, 2021

(54) HYDROPHOBIC GEL BASED ON VITAMIN E FREE FROM SILICONE PRODUCTS FOR TOPICAL APPLICATION

(71) Applicant: BIO.LO.GA. S.R.L., Conegliano (IT)

(72) Inventor: Giorgio Panin, Rovigo (IT)

(73) Assignee: BIO.LO.GA. S.R.L., Conegliano (IT)

( * ) Notice: Subject to any disclaimer, the term of this patent is extended or adjusted under 35 U.S.C. 154(b) by 544 days.

(21) Appl. No.: 15/759,380

(22) PCT Filed: Sep. 19, 2016

(86) PCT No.: PCT/EP2016/072097
§ 371 (c)(1),
(2) Date: Mar. 12, 2018

(87) PCT Pub. No.: WO2017/050668
PCT Pub. Date: Mar. 30, 2017

(65) Prior Publication Data
US 2019/0328626 A1 Oct. 31, 2019

(30) Foreign Application Priority Data
Sep. 25, 2015 (IT) .................. 102015000055392

(51) Int. Cl.
*A61K 8/04* (2006.01)
*A61K 8/36* (2006.01)
*A61K 8/37* (2006.01)
*A61K 8/63* (2006.01)
*A61K 8/67* (2006.01)
*A61K 8/68* (2006.01)
*A61K 8/92* (2006.01)
*A61Q 19/00* (2006.01)

(52) U.S. Cl.
CPC .............. *A61K 8/042* (2013.01); *A61K 8/361* (2013.01); *A61K 8/37* (2013.01); *A61K 8/63* (2013.01); *A61K 8/678* (2013.01); *A61K 8/68* (2013.01); *A61K 8/922* (2013.01); *A61Q 19/00* (2013.01)

(58) Field of Classification Search
CPC . A61K 8/37; A61K 8/042; A61K 8/92; A61K 8/375; A61K 8/678; A61K 2800/34; A61K 8/63; A61K 8/68; A61Q 19/00
USPC ........................................................ 514/458
See application file for complete search history.

(56) References Cited

U.S. PATENT DOCUMENTS

2013/0319889 A1 12/2013 DeSantis
2014/0242020 A1* 8/2014 Meyer .................. A61K 8/9794
424/74

FOREIGN PATENT DOCUMENTS

| CN | 102688162 A | 9/2012 |
|---|---|---|
| EP | 0998943 A1 | 5/2000 |
| FR | 2978661 A1 | 9/2012 |
| WO | 9810793 A1 | 3/1998 |
| WO | 2007003658 A1 | 1/2007 |

OTHER PUBLICATIONS

Busetti et al; title: gelling pearl improves oil-phase viscosity composition in the form of a lipogel for cosmetic; Personal Care; Sep. 2012p.109-111, Sep. 2012. (Year: 2012).*
Unknown author, title: Ceramides in Skin Care: Everything You Need to Know; downloaded from https://thegoodfaceproject.com/articles/ceramides on Nov. 9, 2020.*
International Search Report and Written Opinion for International Application No. PCT/EP2016/072097 (11 Pages) (dated Nov. 16, 2016).

* cited by examiner

*Primary Examiner* — Yanzhi Zhang
(74) *Attorney, Agent, or Firm* — Lucas & Mercanti LLP

(57) ABSTRACT

A hydrophobic gel formulation for topical use, free of silicone products, comprising in weight percentage on the total weight of the formulation: from 10 to 50% of vitamin E, from 20 to 60% of a vegetable butter or a wax, from 10 to 30% triglyceride of caprylic and capric acid and from 3 to 10% of a gelling agent for lipids such as the triglyceride of palmitic and stearic acid.

6 Claims, 1 Drawing Sheet

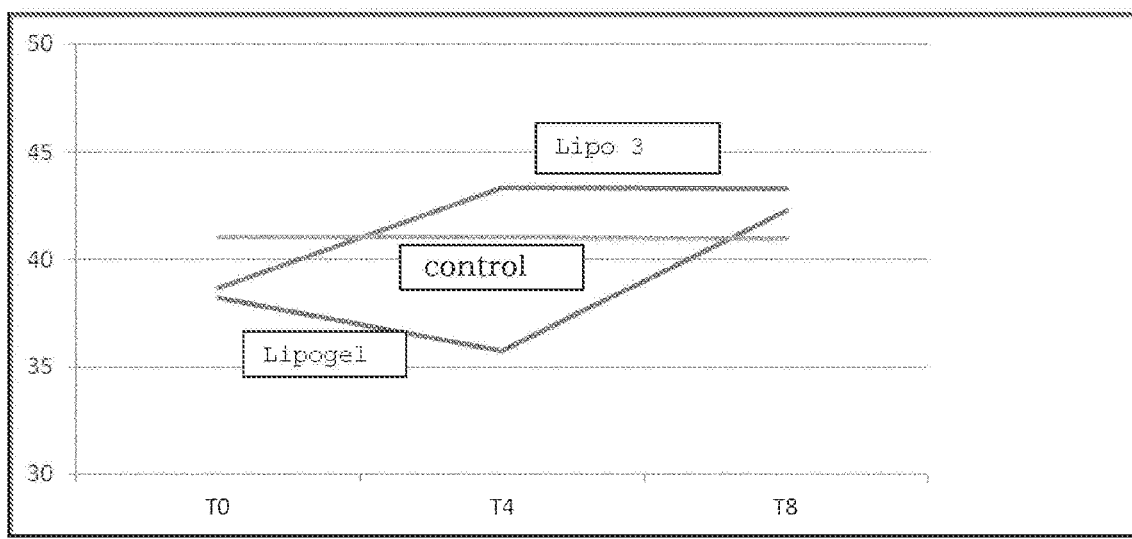

HYDROPHOBIC GEL BASED ON VITAMIN E FREE FROM SILICONE PRODUCTS FOR TOPICAL APPLICATION

CROSS-REFERENCE TO RELATED APPLICATIONS

This application is a 371 of PCT/EP2016/072097, filed Sep. 19, 2016, which claims the benefit of European Patent Application No. 102015000055392, filed Sep. 25, 2015.

FIELD OF THE INVENTION

The present invention generally relates to a formulation for topical use and in particular to a preparation in the form of a hydrophobic gel (lipogel) based on vitamin E, free of silicone products.

PRIOR ART

Vitamin E and derivatives thereof are substances that are widely used in the pharmaceutical and cosmetic industry, by virtue of their antioxidant properties and their scavenging activity towards free radicals, in the preparation of formulations for the treatment of skin diseases, or to combat or prevent skin blemishes.

Vitamin E, particularly in its form of tocopheryl acetate, is easy to spread, is absorbed with surprising rapidity, does not give rise to sensations of heat, leaves the skin soft, elastic and not sticky, and is resistant to cleansing with water or detergents. Moreover, owing to the fact that vitamin E acetate is not a molecule foreign to the human organism, it can easily be integrated in the lipids present in the stratum corneum and can facilitate absorption of substances dispersed therein through the skin.

Cosmetic skin care compositions associating vitamin E with moisturizing substances are widely known: stratum corneum hydration is key for healthy skin, largely determining barrier and permeation/perspiration properties thereof. These compositions have predominantly an aqueous or a hydrolipidic base: e.g. emulsions, aqueous gels, foams, etc., wherein the moisturizing action is exerted by the aqueous component.

There are also topical compositions with a hydrophobic base, i.e. water-free compositions, mainly used for lips care or as balms. In the absence of water in the formulation, moisturization is indirectly obtained herein, by making the treated area more elastic and more permeable to environmental moisture.

For example, patent application FR 2978661 describes a balm almost exclusively consisting of neutral and polar lipids, with small amounts (0.1-2%) of active ingredients, e.g. Vitamin E. Patent application CN 102688162 discloses a gloss formulation including shea butter, triglyceride of caprylic and capric acid and active ingredient in small amounts, e.g. 0.5% of vitamin E. Patent application US 2013/319889 discloses compositions for skin care containing beeswax, cocoa butter, shea butter, a complex mixture of vegetable oils, together with very small amounts of active ingredient, e.g. Vitamin E.

In all the aforementioned publications, the authors did not study the incorporation of high amounts of active ingredient into the composition, nor the resulting compositions stability; in the majority of the cases these are compositions with a highly variable viscosity depending on temperature, with an oily texture when in contact with the skin.

A modern and greatly appreciated form for skin moisturization by means of hydrophobic substances is that consisting of hydrophobic gel or lipo-gel: these are compositions having low viscosity, marginally affected by ambient temperature, easily applicable also onto large skin surfaces, and capable of forming thereon a thin and stable layer that protects skin and maintains the composition on the application site, extending in time the elasticizing and moisturizing effect. Unlike fat-based creams, the lipogel does not have an oily texture when it comes in contact with the skin, therefore giving the user a more pleasant feeling upon application thereof; in particular the lipogel does not tend to fluidize at skin temperature: in fact, its texture is not regulated by the viscosity of the fats therein contained, but by the formation of a three-dimensional molecular lattice (gel) which reduces the density of the product and ensures its structuring in a substantially temperature-independent manner.

For example, application WO 98/10793 to the same applicant describes a hydrophobic gel for topical use, consisting of Vitamin E and a cyclomethicone:dimethiconol mixture in 8:2 ratio by weight, with or without hydrogenated castor oil; in particular two examples of formulation, wherein high quantities of vitamin E (20 or 30% of the composition total weight) have been used in association with a 8:2 cyclomethicone/dimethiconol mixture and optionally 5% hydrogenated castor oil, were provided.

Such gels proved to be excellent formulations for cosmetic use; however, over time, they showed a certain tendency to separate a liquid phase (syneresis).

This issue has been overcome by the hydrophobic gels subsequently described in patent application EP 998 943, on behalf of the Applicant, where stable hydrophobic gels, based on vitamin E acetate, a volatile silicone, and hydrogenated castor oil are described; a limitation for these compositions is represented by the use of significant percentages of synthetic silicone products (cyclomethicone, hexamethyldisiloxane, etc.), which can represent up to 70% by weight of the composition: these are non-natural elements for the skin, possibly related to sensitization events and known cause of environmental toxicity. On the other hand, it is not easy to remove these components, which enable adequate skin moisturization and form stable gels with high amounts of vitamin E. Therefore, there still is the need for new hydrophobic gel formulations, incorporating high amounts of vitamin E, which avoid the use of silicone products and use natural components, same or similar to those naturally occurring in the skin, and which show a high moisturizing activity.

SUMMARY

In view of these needs, the Applicant has now developed a new formulation for topical use in which specific hydrophobic components, in specific concentration ranges, cooperate in a synergistic manner to provide a hydrophobic gel (lipogel) with high amounts of vitamin E, high moisturizing power, without the use of silicone products, and highly akin to skin composition.

The new formulation in question, entirely based on natural substances, comprises, in percentages by weight on the total formulation weight:
- from 10 to 50% of vitamin E,
- from 20 to 60% of a vegetable butter or a wax
- from 10 to 30% of a triglyceride of caprylic and capric acid
- from 3 to 10% of a gelling agent for lipids, such as, e.g. the triglyceride of palmitic and stearic acid.

In experimental tests carried out by the Applicant, the present invention proved to be extremely effective in promoting skin moisturization, with a marked effect after few hours from administration and lasting many hours without the need for new application, even more effective than currently known hydrophobic gels.

DESCRIPTION OF FIGURES

FIG. 1: Skin moisturization test (corneometric evaluation) results after application of the formulation of the present invention (VEA LIPO3) and the reference composition (VEA LIPOGEL), compared with untreated controls.

DETAILED DESCRIPTION

The term "free" of silicone products, as used herein with reference to present formulations, means that said silicone products are absent from the formulations or may be present only in trace amounts or as impurities, not affecting the formulation properties. In turn, the term "silicone products" refers to any polymeric product containing silicon; the term is particularly but not exclusively related to products commonly found in topical compositions, such as silicone, dimethicone, cyclomethicone, dimethiconol, polysiloxanes, etc.

The term "hydrophobic" with reference to the present formulations means that they do not contain water or other aqueous or polar solvent in any state, e.g. free or emulsified, including instead the hydrophobic substances listed in the present invention.

In the present compositions, the content of vitamin E is comprised between 10 and 50%, preferably comprised between 20 and 40%, for example between 25-35% by weight on the composition weight. Vitamin E can be used in all its forms (tocopherols and tocotrienols, isomers (alpha, beta, gamma, delta) and derivatives thereof. The use of vitamin E in the form of tocopheryl acetate is preferred. Vitamin E gives to the present compositions useful skin protective properties, reducing radical oxidation events, preventing aging phenomena, and contributing to skin covering layer softness by means of the product left on the skin after administration.

The vegetable butter used in these formulations can be any of those commonly available, such as butter of: shea, cocoa, almonds, kokum cucpacu, green tea, apricot, orange, lemon, pistachio, coffee, etc. Shea butter is particularly preferred. Wax also can be chosen from among those commonly available; preferred waxes are rice wax and beeswax. Vegetable butter or wax is employed in an amount from 20 to 60%, preferably from 30 to 50%, for example 35-45%.

The triglyceride of caprylic and capric acid (INCI name: (Caprylic/Capric Triglyceride) is a synthetic glycerol triester with C8-C10 acids—caprylic (C8) and capric acid (C10) derived from coconut oil fractionation. It is a colorless to slightly yellow, low viscosity, odourless liquid. It is a good substitute for vegetable oils and is stable to oxidation with respect to the latter because it is completely saturated. It has remarkable emollient properties. This product is employed in the present formulations in an amount comprised between 10 to 30%, preferably between 15 to 25%.

The gelling agent for lipid is a palmitic and stearic acid triglyceride (INCI name: Palmitic/Stearic Triglyceride); alternatively, it can be chosen from among those commonly available, for example Dibutyl Lauroyl Glutamide, Dibutyl Ethylhexanoyl Glutamide, Magnesium/Aluminium/Hydroxide/Carbonate, Magnesium Hydroxide, Zinc Carbonate Hydroxide/Aluminium Hydroxide, silica or methylcellulose polymers. The preferred gelling agent is palmitic and stearic acid triglyceride, which has also emollient and antioxidant skin properties; it is a highly environmentally friendly product, stable to oxidation as it is completely saturated. The product is commercially available from various sources, e.g. under the brand Olifeel® (pearls). This product is employed in the present formulations in an amount comprised between 3 to 10%, preferably between 3 to 9%.

The present formulations may optionally contain a minor amount of ceramide and/or phytosterols. Ceramide is a waxy lipid consisting of sphingosine and fatty acids; it is typically present in the stratum corneum, where it prevents dehydration events and increases the barrier function. Nine natural ceramides are known, all of which can be used according to the invention, either alone or mixed together. Particularly preferred is ceramide-NP (the N-acylated sphingolipid consisting of phytosphingosine (q.v.) having the D-erythro structure linked to normal saturated or unsaturated fatty acid) or ceramide-3, consisting of n-acyl sphingosine and non-hydroxylated fatty acids Phytosterols are a group of plant steroids, with structure similar to cholesterol. Stigmasterol, sitosterol, campesterol, etc., which can be used alone or combined, are typical members of this class. Preferred compositions may comprise from 0.01 to 1% of ceramide (preferably from 0.01 to 0.4%) by weight on total composition. They may further comprise from 0.1 to 2% of phytosterols by weight on total composition.

Optionally, the formulations of the invention may include additional ingredients, either as excipients or further active ingredients. Among the excipients in particular hydrogenated castor oil is mentioned, preferably present as percentage from 1 to 10%, more preferably from 0.1 to 6% by weight of the composition. Additional excipients may be additional hydrophobic components, rheology modifiers, preservatives, perfumes, etc. Further hydrophobic components are, for example, vegetable oils and fatty acids esters such as octyl palmitate, isopropyl myristate and ethyl oleate or mixtures thereof.

The hydrophobic gel according to the invention effectively dissolve or suspend pharmaceutically active principles, also in large quantities.

Examples of active ingredients that can be used (in addition to vitamin E) are: antibiotics, such as gentamicin, neomycin, clindamycin and tetracyclines, corticosteroids, such as hydrocortisone acetate or butyrate, diflucortolone valerate, methylprednisolone aceponate, mometasone furoate and betamethasone esters, trans-retinoic acid, synthetic retinoids, calcipotriol, vitamins such as retinol and its derivatives (retinol acetate and palmitate), ascorbic acid lipophilic derivatives, such as palmitoyl ascorbic acid, vitamin K, vitamin D, vaso-protectors, such as flavonoids and topical anti-inflammatory agents. Lipophilic active substances are preferably used, which effectively dissolve in the current hydrophobic medium; however, the addition of hydrophilic active substances, in this case suspended or otherwise incorporated within the composition, is not excluded.

The invention includes a process for preparing the hydrophobic gel described above; in a most general sense, the process comprises mixing together said vitamin E, vegetable butter or wax, gelling agent and any ceramides, phytosterols and hydrogenated castor oil, in aforementioned percentages thereof.

The invention also covers the use of the previously described hydrophobic lipogel as topical skin moisturizing and protective cosmetic product.

The hydrophobic gel according to the invention has excellent stability, excellent spreadability on skin, and is rapidly absorbed. Following the application of the hydrophobic gel according to the invention, the skin is extremely soft and silky. Compared to the known lipogels, it allows to earlier achieve a substantial moisturizing effect, which is maintained for many hours after application.

For further illustration of the present invention, some non-limiting preparation examples and efficacy proofs of the hydrophobic gel according to the invention are provide hereinafter.

Example 1 Lipogel Preparation

A formulation in accordance with the invention was prepared according to the following composition, where the percentages are intended by weight of the total composition.
tocopheryl acetate: 31%
shea butter: 38%
triglyceride of caprylic and capric acid, 20%
triglyceride of palmitic and stearic acid, 7.0%
ceramide-NP: 0.3%
phytosterols: 0.4%
hydrogenated castor oil. 2.5%

The preparation method is as follows: preparing a first phase comprising Vitamin E, hydrogenated castor oil, phytosterols, ceramides by heating the whole up to 120° C. to obtain a homogeneous solution. In a separate container the missing ingredients are heated up to 60° C. The two phases are then combined together and mixed for about 30 minutes at room temperature.

Example 2: Evaluation of Moisturizing Effect 2.1 Corneometer

The corneometer is a device for measuring the moisture content of the surface layers of epidermis.

It consists of a probe which, resting on the skin area of interest, measures skin surface electrical conductance, which varies depending on skin moisture content.

This means that the device exploits the physical principle whereby the skin surface area (stratum corneum) displays an electrical resistance to the current flow, which is the lower, the more the skin is hydrated. The method is not affected by other components within in the stratum corneum (e.g. salts). The assay is carried out by placing on the skin surface a probe, which is run through by a very weak electric current, and subsequently reading the corresponding conductance value, which is related to the water content of the epidermis at the measuring point.

2.2 Test Objectives

The purpose of the test is the assessment of the moisturizing capability of the composition of example 1 (Vea Lipo) over 8 hours period, compared to untreated subjects (negative control) or to subjects treated with an anhydrous lipogel based on silicone (Vea Lipogel), as reference product described in patent application EP 998 943, par. [0023].

2.3 Materials and Methods

A prototype batch of VEA LIPO3 has been used for the test. The evaluation was performed with Corneometer CM825. The test was performed on 10 volunteers, who have signed and dated Informed Consent and Privacy Policy modules before the assay.

Each volunteer was asked to sit in the laboratory for at least 15 minutes. The investigator performed a measurement of the baseline moisturization level in three areas of both right and left volar forearm, before applying the investigational product. Each area has a size of 5×2 cm. 5 measurements were collected from each area. The mean of the measurements for each area at each time (T0, T4 and T8) has been considered.

After this measurement, the investigator applied:

in an area A: VEA LIPO3 in an area B, different from the previous one: VEA LIPO-GEL a third area C, untreated throughout the duration of the assay, served as a negative control.

Two checks have then been carried out at 4 hour distance. At each check, the volunteer was asked to wait in the room for at least 15 minutes before performing the measurements required in all three areas.

3. Results

An acronym legend used to identify the areas, is depicted below:

A=VEA LIPO3 application area

B=VEA LIPOGEL application area

C=area used as a negative control

T0=mean of 5 measurements carried out before product application

T4=mean of 5 measurements taken 4 hours after first application

T8=mean of 5 measurements taken 8 hours after first application. The values obtained from the measurement carried out at 4 and 8 hours from test start were compared with the baseline measurements (T0).

| Area A: VEA LIPO3 | | | | | |
|---|---|---|---|---|---|
| Volunteer | T0 | T4 | T8 | T4/T0 | T8/T0 |
| 1 | 42.00 | 45.00 | 44.60 | 1.07 | 1.06 |
| 2 | 30.60 | 38.40 | 43.20 | 1.25 | 1.41 |
| 3 | 52.20 | 51.00 | 53.00 | 0.98 | 1.02 |
| 4 | 50.80 | 46.00 | 53.40 | 0.91 | 1.05 |
| 5 | 38.40 | 42.00 | 42.60 | 1.09 | 1.11 |
| 6 | 30.60 | 37.80 | 30.80 | 1.24 | 1.01 |
| 7 | 31.60 | 40.20 | 36.30 | 1.27 | 1.15 |
| 8 | 36.20 | 44.00 | 50.00 | 1.22 | 1.38 |
| 9 | 33.00 | 40.20 | 36.20 | 1.22 | 1.10 |
| 10 | 41.33 | 48.83 | 42.60 | 1.18 | 1.03 |
| Mean | 38.67 | 43.34 | 43.27 | 1.14 | 1.13 |

| Area B: VEA LIPOGEL | | | | | |
|---|---|---|---|---|---|
| Volunteer | T0 | T4 | T8 | T4/T0 | T8/T0 |
| 1 | 33.80 | 34.30 | 33.50 | 1.01 | 0.99 |
| 2 | 34.40 | 39.20 | 44.20 | 1.14 | 1.28 |
| 3 | 51.60 | 48.60 | 44.40 | 0.94 | 0.86 |
| 4 | 58.80 | 48.60 | 58.60 | 0.83 | 1.00 |
| 5 | 40.40 | 30.00 | 44.60 | 0.74 | 1.10 |
| 6 | 32.00 | 24.60 | 35.60 | 0.77 | 1.11 |
| 7 | 30.60 | 30.80 | 32.40 | 1.01 | 1.06 |
| 8 | 35.30 | 34.80 | 52.00 | 0.99 | 1.47 |
| 9 | 30.80 | 22.40 | 36.60 | 0.73 | 1.19 |
| 10 | 34.40 | 43.80 | 41.00 | 1.27 | 1.19 |
| Mean | 38.21 | 35.71 | 42.29 | 0.94 | 1.13 |

| Area C: CONTROL | | | | | |
|---|---|---|---|---|---|
| Volunteer | T0 | T4 | T8 | T4/T0 | T8/T0 |
| 1 | 50 | 50 | 50 | 1 | 1 |
| 2 | 27 | 27 | 27 | 1 | 1 |
| 3 | 47 | 47 | 46 | 1 | 1 |
| 4 | 57 | 57 | 57 | 1 | 1 |
| 5 | 38 | 38 | 39 | 1 | 1 |
| 6 | 29 | 29 | 31 | 1 | 1 |
| 7 | 37 | 37 | 37 | 1 | 1 |
| 8 | 49 | 49 | 52 | 1 | 1 |
| 9 | 37 | 37 | 37 | 1 | 1 |
| 10 | 40 | 40 | 38 | 1 | 1 |
| Mean | 41 | 41 | 41 | 1 | 1 |

The data obtained from VEA LIPO3 and VEA LIPOGEL application area then were compared with data detected within D control area, respectively, obtaining the following results.

| Comparison of VEA LIPO3 and Negative Control at T4 | | | |
|---|---|---|---|
| Volunteer | T4/T0 Lipo3 | T4/T0 control | Lipo3 vs control |
| 1 | 1.07 | 1 | 1.07 |
| 2 | 1.25 | 1 | 1.25 |
| 3 | 0.98 | 1 | 0.98 |
| 4 | 0.91 | 1 | 0.91 |
| 5 | 1.09 | 1 | 1.09 |
| 6 | 1.24 | 1 | 1.24 |
| 7 | 1.27 | 1 | 1.27 |
| 8 | 1.22 | 1 | 1.22 |
| 9 | 1.22 | 1 | 1.22 |
| 10 | 1.18 | 1 | 1.18 |
| Mean | | | 1.14 |

| Comparison of VEA LIPOGEL and Negative Control at T4 | | | |
|---|---|---|---|
| Volunteer | T4/T0 Lipo3 | T4/T0 control | Lipo3 vs control |
| 1 | 1.01 | 1 | 1.01 |
| 2 | 1.14 | 1 | 1.14 |
| 3 | 0.94 | 1 | 0.94 |
| 4 | 0.83 | 1 | 0.83 |
| 5 | 0.74 | 1 | 0.74 |
| 6 | 0.77 | 1 | 0.77 |
| 7 | 1.01 | 1 | 1.01 |
| 8 | 0.99 | 1 | 0.99 |
| 9 | 0.73 | 1 | 0.73 |
| 10 | 1.27 | 1 | 1.27 |
| Mean | | | 0.94 |

The above averaged conductance data are summarized and displayed in graphical form in FIG. 1.

In summary, the results obtained show that VEA LIPO3 after 4 hours has a greater moisturizing effect than VEA LIPOGEL with an overall increase of 21% and causes a moisturization increase of 14% compared to untreated skin.

The greater moisturizing effect of VEA LIPO 3 with respect to VEA LIPOGEL is observed up to 8 hours after application while maintaining a moisturization level higher than that of the baseline (untreated controls). From these data it can reasonably be deduced that VEA LIPO3 is absorbed faster than VEA LIPOGEL, thus exerting faster and more intensively its moisturizing effect.

The invention claimed is:

1. A hydrophobic gel formulation for topical use, free of silicone products, consisting of in weight percentage on the total weight of the formulation:
   from 10 to 50% of vitamin E,
   from 20 to 60% of a vegetable butter or a wax,
   from 10 to 30% of a triglyceride of caprylic and capric acid,
   from 3-9% of a triglyceride of palmitic and stearic acid,
   from 0.01-0.4% of ceramide,
   from 0.1-2% of phytosterols, and
   from 0.1-6% of hydrogenated castor oil.

2. The formulation according to claim 1, wherein
   the vitamin E is present from 20 to 40%,
   the vegetable butter or wax is present from 30 to 50%, and
   the triglyceride of caprylic and curie acid is present from 15 to 25%.

3. The formulation according to claim 1, wherein said vitamin E is tocopheryl acetate, said vegetable butter is shea butter, and said ceramide is ceramide-NP.

4. The formulation according to claim 1, wherein
   the vitamin E is tocopheryl acetate and is present from 25-35%,
   the vegetable butter is shea butter and is present from 35-45%, and
   the triglyceride of caprylic acid and capric acid is present from 15-25%.

5. A process to prepare a hydrophobic gel according to claim 1, comprising mixing said vitamin E, vegetable butter or wax, triglyceride of caprylic and capric acid, gelling agent, and possible ceramide, phytosterols and hydrogenated castor oil, in said percentages thereof.

6. A method for using the formulation according to claim 1, comprising the step of topically applying said formulation to a human skin.

* * * * *